United States Patent
Möhler et al.

(10) Patent No.: US 11,045,449 B2
(45) Date of Patent: Jun. 29, 2021

(54) 3-(5-FLUOROINDOLYL)-4-ARYLMALEIMIDE COMPOUNDS AND THEIR USE IN TUMOR TREATMENT

(71) Applicants: JOHANNES GUTENBERG-UNIVERSITÄT MAINZ, Mainz (DE); 03;UNIVERSITÄTSMEDIZIN DER JOHANNES GUTENBERG-UNIVERSITAT MAINZ, Mainz (DE)

(72) Inventors: Markus Möhler, Mainz (DE); Annett Maderer, Griesheim (DE); Gerd Dannhardt, Mainz (DE); Christopher Ganser, Mainz (DE); Eva Lauermann, Mainz (DE); René Mönnikes, Mainz (DE)

(73) Assignees: JOHANNES GUTENBERG-UNIVERSITÄT MAINZ, Mainz (DE); UNIVERSITÄTSMEDIZIN DER JOHANNES GUTENBERG-UNIVERSITAT MAINZ, Mainz (DE)

( * ) Notice: Subject to any disclaimer, the term of this patent is extended or adjusted under 35 U.S.C. 154(b) by 0 days.

(21) Appl. No.: 16/066,268

(22) PCT Filed: Dec. 28, 2016

(86) PCT No.: PCT/EP2016/082777
§ 371 (c)(1),
(2) Date: Jun. 26, 2018

(87) PCT Pub. No.: WO2017/114863
PCT Pub. Date: Jul. 6, 2017

(65) Prior Publication Data
US 2020/0253930 A1    Aug. 13, 2020

(30) Foreign Application Priority Data

Dec. 30, 2015 (EP) .................................. 15203072

(51) Int. Cl.
| | | |
|---|---|---|
| *A61K 31/40* | (2006.01) | |
| *A61K 31/4025* | (2006.01) | |
| *A61P 35/00* | (2006.01) | |
| *A61K 31/4745* | (2006.01) | |
| *A61K 45/06* | (2006.01) | |

(52) U.S. Cl.
CPC ...... *A61K 31/4025* (2013.01); *A61K 31/4745* (2013.01); *A61K 45/06* (2013.01); *A61P 35/00* (2018.01)

(58) Field of Classification Search
CPC .................................................. A61K 31/4025
See application file for complete search history.

(56) References Cited

U.S. PATENT DOCUMENTS

| | | |
|---|---|---|
| 5,057,614 A | 10/1991 | Davis et al. |
| 5,399,712 A | 3/1995 | Hill |
| 5,721,245 A | 2/1998 | Davis et al. |

FOREIGN PATENT DOCUMENTS

| | | |
|---|---|---|
| EP | 0384349 A1 | 8/1990 |
| EP | 1224932 A1 | 7/2002 |
| EP | 1845094 A1 | 10/2007 |
| WO | 1991013071 A1 | 9/1991 |
| WO | 1995007910 A1 | 3/1995 |
| WO | 1997034890 A1 | 9/1997 |
| WO | 2000021927 A2 | 4/2000 |
| WO | 2000038675 A1 | 7/2000 |
| WO | 2002010158 A2 | 2/2002 |
| WO | 2002038561 A1 | 5/2002 |
| WO | 2003057202 A1 | 7/2003 |
| WO | 2003103663 A2 | 12/2003 |
| WO | 2006006939 A1 | 1/2006 |
| WO | 2006061212 A1 | 6/2006 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
Cohen, "Protein kinases—the major drug targets of the twenty-first century?", Nature Rev. Drug Discovery 1, 309-315 (2002).

(Continued)

*Primary Examiner* — Shawquia Jackson
(74) *Attorney, Agent, or Firm* — Viksnins Harris Padys Malen LLP (57) ABSTRACT

The present invention relates to 3-(5-fluoroindolyl)-4-arylmaleimide compounds and pharmaceutical compositions containing them. The compounds of the present invention are protein kinases (GSK-3beta, VEGFR-2 and FLT-3) with antineoplastic activity. They can therefore be used for the treatment or prevention of tumors, in particular solid tumors.

23 Claims, 2 Drawing Sheets

(56) References Cited

FOREIGN PATENT DOCUMENTS

| WO | 2009071620 | A1 | 6/2009 |
|---|---|---|---|
| WO | 2011073091 | A1 | 6/2011 |
| WO | 2011073092 | A1 | 6/2011 |
| WO | 2012084683 | A1 | 6/2012 |

OTHER PUBLICATIONS

Kim, et al., "Inhibition of vascular endothelial growth factor-induced angiogenesis suppresses tumour growth in vivo", Nature 362, 841-844 (1993).

Lambrechts, et al., "Markers of Response for the Antiangiogenic Agent Bevacizumab", Journal of Clinical Oncology 31(9), 1219-1230 (2013).

Patent Cooperation Treaty, International Searching Authority, Search Report and Written Opinion for PCT/EP2016/082777, 15 pages, dated Apr. 24, 2017.

Peifer, et al., "Design, Synthesis, and Biological Evaluation of 3,4-Diarylmaleimides as Angiogenesis Inhibitors", J Med Chem 49, 1271-1281 (2006).

Peifer, et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors", J Med Chem 51, 3814-3824 (2008).

Peifer, et al., "Profile and Molecular Modeling of 3-(Indole-3-yl)-4-(3,4,5-trimethoxyphenyl)-1H-pyrrole-2,5-dione (1) as a Highly Selective VEGF-R2/3 Inhibitor", J Med Chem 49, 7549-7553 (2006).

Pommier, et al., "Topoisomerase I inhibitors: camptothecins and beyond", Nature Reviews Cancer 6, 789-802 (2006).

Zhang, et al., "3-(7-Azaindolyl)-4-arylmaleimides as potent, selective inhibitors of glycogen synthase kinase-3", Bioorganic & Medicinal Chemistry Letters 14, 3245-3250 (2004).

Zhang, et al., "The significance of combining VEGFA, FLT1, and KDR expressions in colon cancer patient prognosis and predicting response to bevacizumab", Onco Targets and Therapy 8, 835-843 (2015).

\* cited by examiner

3-(5-FLUOROINDOLYL)-4-ARYLMALEIMIDE COMPOUNDS AND THEIR USE IN TUMOR TREATMENT

CROSS-REFERENCE TO RELATED APPLICATION(S)

This patent application claims the benefit of priority of EP Application No. 15203072.2, filed Dec. 30, 2015.

The present invention relates to 3-(5-fluoroindolyl)-4-arylmaleimide compounds, pharmaceutical compositions containing them, and their use in tumor treatment.

BACKGROUND

Protein kinases are an interesting class of target molecules for developing improved cancer therapies. These proteins are known to regulate the majority of cellular pathways including such relevant for control cell growth, cell movement, apoptosis resistance and survival—all processes relevant for cancer growth and progression. In fact, the tyrosine kinases act primarily as growth factor receptors. Receptors for the vascular endothelial growth factor (VEGF), the epidermal growth factor (EGF) and the bood platelet growth factor (PDGF) are particularly interesting targets in the development of tumor therapeutics (Nat. Rev. Drug Discov. 1 (2002) 309-315). The formation of new blood vessels (angiogenesis or neovascularization) are essential for the nutrient and oxygen supply of tumors and, moreover, contributes to metastasis (Nature (1993), 362, 841-844). Therefore, research focused on the strategy to find active compounds which control the regulation of relevant kinases (VEGF and non-VEGF pathway) or the angiogenesis process. This led to the development of moguntinones, a class of small molecule compounds which are 3-(indolyl)- or 3-(azaindolyl)-4-arylmaleimide derivatives with tumor and vascular targeting properties. The moguntinones and their use are disclosed in WO 2006/061212, WO 2009/071620, WO 2011/073091, WO 2011/073092 and WO 2012/084683. The publications of Peifer et al. in J. Med. Chem. 2006, 49: 1271-1281; J. Med. Chem. 2006, 49: 7549-7553; and J. Med. Chem. 2008, 51: 3814-3824 are concerned with the design, synthesis and evaluation of 3,4-diarylmaleimides as angiogenesis inhibitors. WO 02/38561 describes kinase inhibitors of the formula wherein R is an aryl residue such as a hydroxyl substituted phenyl group. Compounds of similar structure are described in EP 328 026 A, WO 02/10158, WO 03/057202, WO 03/095452, WO 03/103663, WO 95/07910, WO 00/38675, WO 97/34890, WO 91/13071, EP 384 349 A, EP 540 956, EP 1 224 932 A, WO 00/021927, and Bioorganic & Medicinal Chemistry Letters 14 (2004), 3245-3250.

EP 1 845 094 A and WO 2006/06939 describe the kinase inhibitor of formula:

and related compounds for use in treating cancer.

The above-mentioned strategy has been realized with bevacizumab in combination with a tyrosin kinase inhibitor (J. Clin. Oncol. 2013, 31, 1219-1230; Onco Targets and Therapy, 2015, 8, 835-843). In a combination of two active compounds having different targets the compounds may interact with regard to potency, metabolization and excretion. Furthermore, there may be differences in absorption and half-life period. Thus, a therapy with two active compounds having different targets is difficult to control.

The problem underlying the invention was therefore to provide compounds which are useful in a single therapy and provide the desired effectiveness and compatibility.

SUMMARY OF THE INVENTION

The present invention relates to compounds of formula I:

(I)

wherein
$R^1$ is methoxy or hydroxyl; and
$R^2$ is 2-amino-4-methylbutanoyloxyethyl ($(CH_3)_2CHCH_2CH(NH_2)C(O)OCH_2CH_2$—), 2-amino-4-methylbutanoyloxypropyl, hydroxyethyl, hydroxypropyl or H;
with the proviso that, if $R^2$ is H, $R^1$ is hydroxyl;
and the physiologically acceptable salts, solvates and solvates of the salts of the compounds of formula I.

DETAILED DESCRIPTION OF THE INVENTION

An embodiment of the invention is a compound having formula (I) wherein $R^1$ is methoxy and $R^2$ is 2-amino-4-methylbutanoyloxyethyl, 2-amino-4-methylbutanoyloxypropyl, hydroxyethyl, or hydroxypropyl and the physiologically acceptable salts, solvates and solvates of the salts of the compounds of formula I.

A further embodiment is compound having formula (I) wherein $R^1$ is hydroxy and $R^2$ is hydroxyethyl, hydroxypropyl or H, and the physiologically acceptable salts, solvates and solvates of the salts of the compounds of formula I.

A further embodiment is compound having formula (I) wherein $R^1$ is methoxy or hydroxyl and $R^2$ is hydroxyethyl or hydroxypropyl, and the physiologically acceptable salts, solvates and solvates of the salts of the compounds of formula I.

Further embodiments are the compounds of formulae (Ia), (Ib), (Ic), (Id), (Ie), (If) and (Ig):

(Ia)

2-(3-(2,5-Dioxo-4-(3,4,5-trimethoxyphenyl)-2,5-dihydro-1H-pyrrol-3-yl)-5-fluoro-1H-indol-1-yl)-ethyl-2-amino-4-methylpentanoate;

(Ib)

3-(5-fluoro-1-(2-hydroxyethyl)-1H-indol-3-yl)-4-(3,4,5-trimethoxyphenyl)-maleimide;

(Ic)

3-(5-fluoro-1-(2-hydroxyethyl)-1H-indol-3-yl)-4-(4-hydroxy-3,5-dimethoxyphenyl)-maleimide;

(Id)

3-(5-fluoro-1H-indol-3-yl)-4-(4-hydroxy-3,5-di methoxyphenyl)-maleimide;

(Ie)

3-(3-(2,5-Dioxo-4-(3,4,5-trimethoxyphenyl)-2,5-dihydro-1H-pyrrol-3-yl)-5-fluoro-1H-indol-1-yl)-propyl-2-amino-4-methylpentanoate;

(If)

3-(5-fluoro-1-(3-hydroxypropyl)-1H-indol-3-yl)-4-(3,4,5-trimethoxyphenyl)-maleimide;

(Ig)

3-(5-fluoro-1-(3-hydroxypropyl)-1H-indol-3-yl)-4-(4-hydroxy-3,5-dimethoxyphenyl)-maleimide;

and the physiologically acceptable salts, solvates and solvates of the salts of the compounds of formula (Ia), (Ib), (Ic), (Id), (Ie), (If) and (Ig).

Physiologically acceptable salts of the compounds of formula I include acid addition salts with physiologically acceptable acids. Examples of suitable physiologically acceptable organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzene sulfonic acid and toluene sulfonic acid, carboxylic acids, such as acetic acid, and hydroxycarboxylic acids, such as oxalic acid, malonic acid, maleic acid, mandelic acid, ascorbic acid, fumaric acid, gluconic acid, lactic acid, tartaric acid, citric acid, glycolic acid, adipic acid and benzoic acid. Other utilizable acids are described, e.g., in "Fortschritte der Arzneimittelforschung" [Advances in drug research], Volume 10, pages 224 ff., Birkhäuser Verlag, Basel and Stuttgart, 1966.

The physiologically acceptable salts of the compounds of formula I also include salts of a physiologically tolerated anion, e.g. a deprotonated physiologically acceptable acid, with a compound of formula I, wherein one or more than one nitrogen atom may be quaternized, e.g. with an alkyl residue (e.g. methyl or ethyl).

Physiologically acceptable solvates are in particular hydrates.

The compounds of the present invention can be prepared according to the methods given in the examples section.

The compounds of the present invention have antineoplastic activity. The particular advantage is that the compound of formula Ia (or Ib) can be used for a "sequential" therapy because it is metabolized via compound Ib which is further metabolized to compound Ic and then to compound Id. A further metabolic pathway is from compound Ia via compound Ib to a compound of formula I wherein $R^1$ is methoxy and $R^2$ is H and further to compound Id. The compounds of the invention address different kinases allowing a "combination" therapy with one single compound.

The compounds of the invention can therefore be used for the treatment or prevention of tumors, in particular solid tumors, such as astrocytoma, bladder cancer, bone cancer, brain tumor, breast cancer, bronchial tumor, cervical cancer, colorectal cancer, endometrial cancer, esophageal cancer, gallbladder cancer, gastrointestinal stromal tumor, germ cell tumor, glioma, head and neck cancer, liver cancer, lymphoma, sarcoma, lung cancer, melanoma, ovarian cancer, pancreatic cancer, thyroid cancer, neuroblastoma, prostate cancer, renal cancer, skin cancer, squamous neck cancer, stomach (gastric) cancer, testicular cancer. The compounds of the invention are especially useful for treatment or prevention of cervical cancer, colorectal cancer, gastrointestinal stromal tumor, liver cancer, lung cancer, ovarian cancer, prostate cancer, stomach cancer, and pancreatic carcinoma.

According to a further embodiment, the compounds of the present invention can be used for the treatment or prevention of leukemia. Leukemia according to the present invention comprises in particular acute lymphocytic leukemia (also known as acute lymphoblastic leukemia, or ALL), acute myelogenous leukemia (also known as acute myeloid leukemia, or AML); chronic lymphocytic leukemia (CLL), mixed-lineage leukemia and chronic myelogenous leukemia (CML). These leukemias and further subtypes of these leukemias are defined by morphological, histochemical and immunological techniques that are well known by those skilled in the art.

In a further embodiment, the invention relates to the treatment of AML or ALL.

In a further embodiment of the invention, the leukemia is characterized by leukemic cells which are positive for expression of FLT3. In a particular embodiment of the invention, the leukemia is characterized by leukemic cells which show enhanced expression of FLT3, compared to non-malignant cells of the same cell type.

The compounds of the invention may be used together with one or more than one other chemotherapeutic agent. A further embodiment of the invention is therefore a combination of the compounds of the present invention with one or more than one chemotherapeutic agent including antineoplastic agents, multidrug resistance reversing agents; and biological response modifiers, and combinations thereof, examples being given below. The combination of the invention exhibits enhanced tumor activity.

Suitable antineoplastic agents may be selected from the group comprising compounds affecting integrity and synthesis of DNA, e.g. topoisomerase I inhibitors; alkylating agents: intercalating agents or DNA-binding antibiotics; antimitotic compounds such as taxanes: vinca alkaloids or colchicine derivatives; compounds for targeted cancer therapy such as protein kinase inhibitors, antibodies binding to cell membrane receptors and soluble decoy receptors; compounds affecting the cell metabolism, e.g. farnesyltransferase inhibitors, purine or pyrimidine analogues.

Examples for antineoplastic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifarnib.

Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, axitinib, neratinib, vatalanib, pazopanib, midostaurin and enzastaurin.

Examples for antineoplastic agents which are antibodies comprise trastuzumab, cetuximab, panitumumab, rituximab, bevacizumab, mapatumumab, conatumumab, lexatumumab and the like.

An example for a multidrug resistance reversing agent is PSC 833, a potent inhibitor of the efflux of antitumor drugs mediated by P-glycoprotein.

Suitable biological response modifiers may be selected from the group consisting of monoclonal antibodies and cytokines, such as interferons, interleukins and colony-stimulating factors, e.g., rituxan, CMA-676, interferon-alpha recombinant, interleukin-2, interleukin-3, erythropoetin, epoetin, G-CSF, GM-CSF, filgrastim, sargramostim and thrombopoietin.

According to a particular embodiment, the further chemotherapeutic agent is a topoisomerase I inhibitor and especially camptothecin or a derivative thereof such as described by Pommier, Y. (2006), Nature Reviews Cancer 6: 789-802. Examples for topomerase I inhibitors comprise compounds and the pharmaceutically acceptable salts thereof such as irinotecan (in particular irinotecan hydrochloride), topotecan (in particular topotecan hydrochloride), rubitecan, exatecan (in particular exatecan mesylate), lurtotecan, gimatecan, prothecan, karenitecin, belotecan (in particular belotecan hydrochloride), silatecan or diflomotecan and the salts thereof. Preferred is irinotecan (in particular irinotecan hydrochloride) or topotecan (in particular topotecan hydrochloride), and especially irinotecan (in particular irinotecan hydrochloride).

The weight ratio of the compounds of the invention to the chemotherapeutic agent is in general in the range from 5:1 to 1:500, in particular 3:1 to 1:200.

A further embodiment of the invention is a pharmaceutical composition comprising at least one compound of formula I. In a further embodiment the composition comprises at least one additional chemotherapeutic agent as defined above. In general, the pharmaceutical compositions comprise an amount therapeutically effective for tumor treatment of at least one compound of formula I as defined herein.

A further embodiment of the invention is a compound of formula I for use in a method of treating tumors by administration of a compound of the invention to a subject, preferably a human subject, in need of such treatment.

According to a further embodiment, said method comprises the use of an additional therapeutic agent (other than a compound of formula I). The additional therapeutic agent may be as defined above and can be administered prior to, simultaneously with or after administration of a compound of the invention.

For use the compounds or combinations of the present invention can be incorporated into standard pharmaceutical dosage forms. For example, the compounds or combinations are useful when administered in systemic or local, oral or parenteral applications and for this purpose are combined with the usual pharmaceutical excipients, diluents and adjuvants, e.g., organic and inorganic inert carrier materials such as water, gelatin, lactose, starch, magnesium stearate, talc, vegetable oils, gums, polyalkyleneglycols, etc. These pharmaceutical preparations can be employed in a solid form, e.g., as tablets, capsules, and especially in combination with or for admixture with a palatable food item suitable for mammals; or they can be administered in liquid form, e.g., as solutions and elixirs. Pharmaceutical excipients and adjuvants which can be added to include preservatives, antioxidants, antimicrobial agents and other stabilizers; wetting, emulsifying, and suspending agents, and anticaking compounds; fragrance and coloring additives; compositions for improving compressibility, or to create a delayed-, sustained-, or controlled-release of the active ingredient; and various salts to change the osmotic pressure of the pharmaceutical preparation or to act as buffers.

The therapeutically effective amount of a compound of formula I as defined may be administered systemically to said mammal, wherein said systemic administration comprises: (1) injection or infusion into suitable body tissues or cavities of a pharmaceutical composition containing said compound or combination in suitable liquid form such as aqueous solutions, emulsions or suspensions for intraarterial, intra- or transdermal (including subcutaneous) and most commonly intramuscular or intravenous delivery thereof; or for serving as a depot for delivery thereof; (2) instillation into suitable body tissues or cavities of a pharmaceutical composition containing said compound or combination in suitable solid form, e.g., comprising a matrix of bio-compatible and bio-erodible materials in which particles of at least one compound of formula I are dispersed for serving as a solid implant composition for delayed-, sustained-, and/or controlled-release delivery thereof; or (3) ingestion or administration of a pharmaceutical composition containing said compound or combination in suitable solid or liquid form for transdermal delivery thereof, for instance a transdermal patch or a subepidermal (subcuticular) implant, for peroral delivery thereof.

The dosage forms described herein may be formulated so as to provide controlled-, sustained-, and/or delayed release of the active ingredient from said dosage form.

Preferred peroral dosage forms for systemic administration are solids, e.g., palatable oral compositions such as fast dissolving palatable wafers, tablets, capsules, caplets, etc., and liquids, e.g., solutions, suspensions, emulsions, etc. Pharmaceutical compositions of special types suitable for oral administration to mammals may be used, and include, but are not limited to such items as an oral paste to be delivered to the back of the tongue of the mammal being treated, a granular form to be delivered through incorporation in the mammal's food, and a chewable form wherein the active ingredient is consumed along with the palatable chew, or a chewable form which may deliver the active ingredient by leaching from the body of the chew which is not consumed, during mastication by the mammal being treated. Tablets and capsules are preferred dosage forms.

Said therapeutically effective amount of a compound of formula I as defined may also be administered locally to said mammal, wherein said local administration comprises: (1) injection or infusion into a local site affected with abnormal angiogenesis and/or vascular dysfunction of a pharmaceutical composition containing said compound of formula I or combination in suitable liquid form for delivery thereof, including components which provide delayed-release, controlled-release, and/or sustained-release of said compound or combination into said local site; or for serving as a depot for delivery thereof wherein said composition provides storage of said compound or combination and thereafter delayed-, sustained-, and/or controlled-release thereof; or (2) instillation of a pharmaceutical composition containing said compound or combination in suitable solid form for serving as a solid implant for delivery thereof, said composition optionally providing delayed-, sustained-, and/or controlled-release of said compound or combination to said local site.

The therapeutically effective amount of the compound of formula I is administered to a mammal to be treated in an amount expressed as milligrams per $m^2$ of body surface of said mammal, per day: "mg/$m^2$/day". The dose, i.e., the therapeutically effective amount of a compound of formula I will usually range from about 0.2 mg/$m^2$/day to about 2000 mg/$m^2$/day, preferably from about 0.5 mg/$m^2$/day to about 1500 mg/$m^2$/day, more preferably from about 1.0 mg/$m^2$/day to about 1000 mg/$m^2$/day. In case of a combination of a compound of formula I with a chemotherapeutic agent such as an anticancer agent, administration may be simultaneously, for example given as coformulation or separately, or sequentially. The dose of a compound of formula I will usually be as given above whereas the dose of the chemotherapeutic agent will range from about 0.2 mg/$m^2$/day to about 2000 mg/$m^2$/day, preferably from about 0.5 mg/$m^2$/day to about 1500 mg/$m^2$/day, more preferably from about 1.0 mg/$m^2$/day to about 1000 mg/$m^2$/day.

It is necessary for the skilled artisan, not only to determine the preferred route of administration and the corresponding dosage form and amount, but said artisan must also determine the dosing regimen, i.e., the frequency of dosing. In general terms it is most likely that the choice will be between once-a-day (s.i.d.) dosing and twice-a-day (b.i.d.) dosing, and that the former will provide more rapid and profound therapy, while the latter will provide less profound but more sustained therapy.

The following examples illustrate the invention without limiting it.

EXAMPLES

Infrared spectra were recorded on a Thermo Nicolet Avatar 330 FT-IR spectrometer. 1H (300 MHz, digital resolution 0.3768 Hz) and 13C (75 MHz, digital resolution 1.1299 Hz) NMR were recorded on a Bruker AC 300: the data are reported as follows: chemical shift in ppm from Me$_4$Si as external standard, multiplicity and coupling constant (Hz). EI-Mass spectra were recorded on a Varian MAT 44S (80 eV) and FD-Mass spectra on a Finnigan MAT 7 (5 kV). For clarity purposes only the highest measured signal is given for FD-Mass spectra. Elemental analyses were performed on a Haereus CHN rapid, Carlo Erba Strumentazione 1106. Combustion analyses agreed with the calculated data within ±0.4 unless otherwise stated. Melting points (mp.)/decomposition temperatures were determined on a Büchi apparatus according to Dr. Tottloi and are uncorrected. Where appropriate, column chromatography was performed for crude precursors with Merck silica gel 60 (0.063-0.200 mm). Column chromatography for test compounds was performed using a MPLC-System B-680 (Büchi) with Merck silica gel (0.015-0.040 mm). The progress of the reactions was monitored by thin layer chromatography (TLC) performed with Merck silica gel 60 F-254 plates. Where necessary, reactions were carried out in a nitrogen atmosphere using 4 Å molecular sieves. All reagents and solvents were obtained from commercial sources and used as received.

ABBREVIATIONS rt room temperature
DMF dimethylformamide
DMAP dimethylaminopyridine
DCM dichloromethane
THF tetrahydrofurane
DMSO dimethylsulfoxide
PE/EE petrol ether/ethyl acetate
Mp melting point Example 1

2-(3-(2,5-Dioxo-4-(3,4,5-trimethoxyphenyl)-2,5-dihydro-1H-pyrrol-3-yl)-5-fluoro-1H-indol-1-yl)-ethyl-2-amino-4-methylpentanoate (1) 2-Bromoethoxy-tert-butyldimethylsilane A modified procedure of Galka et al., *J. Lab. Comp. Rad.* 2005, 48, 11, 797-809 was used to prepare the title compound. A mixture of 2-bromoethanol (40 mmol), tert-butyldimethylsilylchloride (40 mmol) and imidazole (44 mmol) was stirred at rt for 3 hours under inert atmosphere. The reaction was quenched with water and extracted with diethylether. The organic layer was dried over MgSO$_4$, filtered and concentrated in vacuo. The purification was achieved by column chromatography (PE/EE) to yield the title compound (36.4 mmol; 91%). $^1$H NMR (300 MHz, CDCl$_3$) δ [ppm]=3.91 (t; $^3$J=6.5 Hz; 2H; OCH$_2$); 3.41 (t; $^3$J=6.5 Hz; 2H; CH$_2$Br); 0.93 (s; 9H; C(CH$_3$)$_3$); 0.11 (s; 6H; 2×CH$_3$).

(2) Ethyl-2-(5-fluoro-1H-indole)-2-oxoacetate

To a solution of 5-fluoroindole (16.28 mmol) in diethylether was added slowly at 0° C. pyridine (170 μl) and ethylchlorooxoacetate (19.8 mmol) under inert gas. The reaction mixture was stirred for 1 h at 0° C., then for 4 h at rt. The precipitate was filtered and washed with water and ethanol (0° C.) to yield the title compound as colorless crystals (11 mmol; 66%). $^1$H NMR (300 MHz, CDCl$_3$) δ [ppm]=9.22 (bs, 1H; NH); 8.53 (d; J=3.3 Hz; 1H; indole-H); 8.11 (dd; J=2.5 Hz; J=9.0 Hz; 1H; indole-H); 7.41 (dd; J=4.3

Hz; J=9.0 Hz; 1H; indole-H); 7.06 (dt; J=2.5 Hz; J=9.0 Hz; 1H; indole-H); 4.41 (q; $^3J$=7.1 Hz; 2H; OC$\underline{H_2}$CH$_3$); 1.43 (t; $^3J$=7.1 Hz; 3H; OCH$_2\underline{CH_3}$).

(3) Ethyl 2-(1-(3-(tert-butyldimethylsilyloxy)-ethyl)-5-fluoro-1H-indol-3-yl)-2-oxoacetate A modified procedure of Faul et al., *J. of Org. Chem*, 1998, 63, 6, 1961-1973 and Zhang et al., *Bioorg. Med. Chem. Lett.*, 2004, 14, 12, 3245-3250 was used. A stirred suspension of ethyl-2-(5-fluoro-1H-indole)-2-oxoacetate (2) (4.3 mmol), CsCO$_3$ (5.6 mmol) and 2-bromoethoxy-tert-butyldimethylsilane (1) (4.7 mmol) in dry DMF was heated to 75-80° C. under nitrogen for 8 hours. The reaction was cooled to rt, diluted with ethyl acetate (40 ml) and filtered. The mixture was washed with water, dried over MgSO$_4$, filtered, concentrated and purified by column chromatography to obtain the title compound as orange oil (12.5 mmol; 78%). $^1$H NMR (300 MHz, CDCl3) δ [ppm]=8.44 (s, 1H, Indol-H), 8.12 (m, 1H, Indol-H), 7.30 (m, 1H, Indol-H), 7.06 (Indol-H), 4.40 (q, J=7.1 Hz, 2H, C$\underline{H_2}$—CH$_3$), 4.27 (t, J=5.0 Hz, 2H, N—C$\underline{H_2}$—CH$_2$—O), 3.95 (t, J=5.0 Hz, 2H, N—CH$_2$—C$\underline{H_2}$—O), 1.44 (t, J=7.1 Hz, 3H, CH$_2$—C$\underline{H_3}$), 0.80 (s, 9H, C(CH$_3$)$_3$), −0.16 (s, 6H, Si(CH$_3$)$_2$).

(4) 3,4,5-Trimethoxyphenylacetamide

A mixture of 3,4,5-trimethoxyphenylacetic acid (10 mmol) and phosphorus pentachloride (10 mmol) in dry DCM was stirred under inert gas. After 2 h, 10 ml of ammonia (25%) was added via syringe and after an additional 1 h the mixture was quenched with ice (100 ml), acidified (10% HCl) and extracted with DCM. The organic fraction was dried (MgSO$_4$) and concentrated, then the crude product was recrystallized in ethanol to obtain the title compound as colorless powder (8.5 mmol; 85%). $^1$H NMR (300 MHz, DMSO) δ [ppm]=7.39 (bs; 1H; NH); 6.87 (bs; 1H; NH); 6.55 (s; 2H; Ar—H); 3.73 (s; 6H; 2×OCH$_3$); 3.61 (s; 3H; OCH$_3$); 3.28 (s; 2H; CH$_2$).

(5) 3-(1-(2-(tert-Butyldimethylsilyloxy)-ethyl)-5-fluoro-1H-indol-3-yl)-4-(3,4,5-trimethoxyphenyl)-maleimide A modified procedure of Peifer et al., WO 2006/061212 and *J. Med. Chem.*, 2006, 49, 4, 1271-1281 was used to prepare 3-phenyl-4-indolyl-maleinimides.

To a solution of ethyl 2-(1-(3-(tert-butyldimethylsilyloxy)-ethyl)-5-fluoro-1H-indol-3-yl)-2-oxoacetate (3) (3.2 mmol) and 3,4,5-trimethoxyphenylacetamid (4) (3.2 mmol) in THF (inert gas, activated molecular sieve 4 Å) was added slowly potassium tert-butoxide (14 mmol) in THF via syringe. The mixture was stirred for 2 h at rt, then diluted with ethyl acetate and filtered. After washing with water, the organic layer was dried over MgSO$_4$, concentrated and purified by column chromatography (PE/EE) to obtain the title compound as orange solid (1.3 mmol; 41%). $^1$H NMR (300 MHz, CDCl3) δ [ppm]=8.09 (s, 1H, Indol-H), 7.34 (s, 1H, Imid-H), 7.29 (m, 1H, Indol-H), 6.90 (m, 1H, Indol-H), 6.74 (s, 2H, Ar—H), 5.99 (m, 1H, Indol-H), 4.29 (t, J=5.0 Hz, 2H, N—C$\underline{H_2}$—CH$_2$—O—), 3.97 (t, J=5.1 Hz, 2H N—CH$_2$—C$\underline{H_2}$—O—), 3.88 (s, 3H, OCH$_3$), 3.56 (s, 6H, 2×OCH$_3$), 0.80 (s, 9H, C(CH$_3$)$_3$), −0.14 (s, 6H, Si(CH$_3$)$_2$).

(6) 3-(5-Fluoro-1-(2-hydroxyethyl)-1H-indol-3-yl)-4-(3,4,5-trimethoxyphenyl)-maleimide To 3-(1-(2-(tert-butyldimethylsilyloxy)-ethyl)-5-fluoro-1H-indol-3-yl)-4-(3,4,5-trimethoxyphenyl)-maleimide (5) (0.91 mmol) in THF was added tetrabutylammoniumfluoride (1.3 mmol) and the mixture was stirred at rt. After completion (TLC), the mixture was dried (MgSO$_4$), concentrated and purified by column chromatography (PE/EE) to obtain the title compound as orange solid (0.84 mmol; 92%). Mp 175° C.; IR ṽ [cm$^{-1}$]=3468, 3276, 2990, 1695, 1491, 1327, 1123, 751. FD-MS m/z (rel. Int.)=440.1 (100%; M$^+$). $^1$H NMR (300 MHz, CDCl3) δ [ppm]=8.05 (s, 1H, Indol-H), 7.40 (s, 1H, Imid-H), 7.28 (m, 1H, Indol-H), 6.92 (m, 1H, Indol-H), 6.75 (s, 2H, Ar—H), 6.08 (m, 1H, Indol-H), 4.34 (t, J=4.7 Hz, 2H, N—C$\underline{H_2}$—CH$_2$—OH), 4.04 (t, J=4.8 Hz, 2H, N—CH$_2$—C$\underline{H_2}$—OH), 3.87 (s, 3H, OCH$_3$), 3.56 (s, 6H, 2×OCH$_3$). $^{13}$C-NMR (75 MHz, DMSO) δ [ppm]=172.56 ($C_q$), 172.33 ($C_q$), 155.62 ($C_q$), 152.59 (2×$C_q$), 138.76 ($C_q$), 133.45 (CH), 131.62 ($C_q$), 128.74 ($C_q$), 125.76 ($C_q$), 125.27 ($C_q$), 108.08 (2×CH), 107.04 (CH), 106.72 ($C_q$), 103.74 (2×CH), 60.50 (CH$_3$), 60.37 (CH2), 55.97 (2×CH$_3$), 49.33 (CH$_2$). Anal. calcd for C$_{23}$H$_{21}$FN$_2$O$_6$×H$_2$O: C, 62.72; H, 4.81; N, 6.36. Found: C, 62.72; H, 4.88; N, 6.18.

(7) 2-(3-(2,5-Dioxo-4-(3,4,5-trimethoxyphenyl)-2,5-dihydro-1H-pyrrol-3-yl)-5-fluoro-1H-indol-1-yl)-ethyl-2-((tert-butoxycarbonyl)-amino)-4-methylpentanoate To a stirred solution of 1-ethyl-3-(3-dimethylaminopropyl)carbodiimid (EDCI; 1.3 mmol) and dimethylaminopyridine (DMAP; 0.22 mmol) in dry DCM, 3-(5-fluoro-1-(2-hydroxyethyl)-1H-indol-3-yl)-4-(3,4,5-trimethoxyphenyl)-maleimide (6) (0.45 mmol) in dry DCM was slowly added via syringe. The reaction mixture was stirred for 24 h at ambient temperature. After quenching with water and extracting with ethyl acetate, the combined organic layers were dried over MgSO$_4$, filtered, concentrated and purified by column chromatography (PE/EE) to obtain the title compound as orange solid (0.4 mmol; 89%). $^1$H NMR (300 MHz, CDCl3) δ [ppm]=8.05 (s, 1H, Indol-H), 7.47 (s, 1H, Imid-H), 7.29 (m, 1H, Indol-H), 6.96 (m, 1H, Indol-H), 6.75 (s, 2H, Ar—H), 6.08 (d, J=12.67 Hz, 1H, Indol-H), 5.00 (d, J=8.75 Hz, 1H, —NH—C$\underline{H}$—CO), 4.48 (m, 4H, —C$\underline{H_2}$—CH$_2$—O—), 3.87 (s, 3H, OCH$_3$), 3.56 (s, 6H, 2×OC$\underline{H_3}$), 1.68 (m, 4H, —N$\underline{H}$—CH—CO and —CH$_2$—C$\underline{H}$(CH$_3$)$_2$, 1.42 (s, 9H, C(C$\underline{H_3}$)$_3$), 0.87 (m, 6H, —CH$_2$—CH(C$\underline{H_3}$)$_2$.

(8) 2-(3-(2,5-Dioxo-4-(3,4,5-trimethoxyphenyl)-2,5-dihydro-1H-pyrrol-3-yl)-5-fluoro-1H-indol-1-yl)-ethyl-2-amino-4-methylpentanoate To 2-(3-(2,5-dioxo-4-(3,4,5-trimethoxyphenyl)-2,5-dihydro-1H-pyrrol-3-yl)-5-fluoro-1H-indol-1-yl)-ethyl-2-((tert-butoxycarbonyl)-amino)-4-methylpentanoate (7) (0.4 mmol) in DCM was added trichloroacetic acid (15 mmol) and the mixture was stirred under inert gas at ambient temperature for 24 h. The solution was then diluted with ethyl acetate (0° C.) and washed three times with saturated NaHCO₃-solution (0-5° C.). The dried organic phase (MgSO₄) was concentrated (water bath 25° C.) to give the title compound as orange-red solid (0.36 mmol; 90%). Mp 180° C.; IR ṽ [cm$^{-1}$]=3673, 2978, 2888, 1703, 1495, 1384, 1119, 959. $^1$H NMR (300 MHz, DMSO) δ [ppm]=11.13 (s; 1H; Imid-NH), 8.44 (s; 3H; —NH$_3^+$), 8.19 (s; 1H; Indol-H), 7.67 (d, J=9.0 Hz; 1H; Indol-H), 7.03 (t; J=9.0 Hz; 1H; Indol-H), 6.67 (s; 2H; Ar—H), 5.88 (d; J=10.6 Hz; 1H; Indol-H), 4.47 (m; 4H, —CH$_2$CH$_2$—), 3.84 (t; J=6.9 Hz; 1H; —NH—C̲H̲—CO—), 3.66 (s; 3H; OCH$_3$), 3.34 (s; 6H; 2×OCH$_3$), 1.60 (m; 1H; —CH$_2$—C̲H̲(CH$_3$)$_2$), 1.45 (dd; J=12.3; 6.8 Hz; 2H; —CH—C̲H̲$_2$—CH—), 0.72 (m, 6H; —CH$_2$—CH(C̲H̲$_3$)2). Anal. calcd for C$_{29}$H$_{32}$FN$_3$O$_7$×HCl× H$_2$O: C, 57.28; H, 5.80; N, 6.91. Found: C, 57.08; H, 6.03; N, 6.56.

The compound (Ie) was prepared in an analogous manner by using 3-bromopropoxy-tert-butyldimethylsilane in place of 2-bromoethoxy-tert-butyldimethylsilane.

Example 2

3-(5-Fluoro-1-(2-hydroxyethyl)-1H-indol-3-yl)-4-(4-hydroxy-3,5-dimethoxyphenyl)-maleimide To aluminium chloride (35 mmol) in DCM was added slowly 3-(5-fluoro-1-(2-hydroxyethyl)-1H-indol-3-yl)-4-(3,4,5-trimethoxyphenyl)-maleimide (6) (1.13 mmol) in DCM and the mixture was stirred for 48 h at ambient temperature. After completion, 20 ml of ice was added (0-3° C.) and the mixture was extracted with ethyl acetate. The organic phase was washed with water and brine, dried over MgSO₄ and concentrated to afford the product as orange crystals (0.9 mmol; 80%). Mp 233° C. FD-MS m/z (rel. Int.)=426.1 (100%; M⁺). $^1$H NMR (300 MHz, CDCl$_3$) δ [ppm]=8.00 (s, 1H, Indol-H), 7.31 (s, 1H, Imid-NH), 6.96 (m, 2H, Indol-H), 6.86 (s, 2H, Ar—H), 6.24 (m, 1H, Indol-H), 5.74 (s, 1H, Ar—OH), 4.36 (m, 2H, N—C̲H̲$_2$—CH$_2$—OH), 4.06 (t, J=5.1 Hz, 2H, N—CH$_2$—C̲H̲$_2$—OH), 3.60 (s, 6H, 2×OCH$_3$). Anal. calcd for C$_{22}$H$_{19}$FN$_2$O$_6$: C, 61.97; H, 4.49; N, 6.57. Found: C, 61.55; H, 4.79; N, 6.38.

Compound (Ig) was prepared in an analogous manner by using 3-(5-fluoro-1-(3-hydroxypropyl)-1H-indol-3-yl)-4-(3, 4,5-trimethoxyphenyl)-maleimide as starting material.

Example 3

(1) 3-(5-Fluoro-1H-indol-3-yl)-4-(4-hydroxy-3,5-dimethoxyphenyl)-maleimide

To a solution of ethyl-2-(5-fluoro-1H-indole)-2-oxoacetate (2) (3 mmol) and 3,4,5-trimethoxyphenylacetamide (4) (3 mmol) in THF (inert gas, activated molecular sieve 4 Å) was added slowly potassium tert-butoxide (14 mmol) in THF via syringe. The reaction mixture was stirred for 2 h at rt, diluted with ethyl acetate and filtered. After washing with water, the organic layer was dried, concentrated and purified by column chromatography (PE/EE) to obtain the title compound as orange solid (1.2 mmol; 40%). Mp=232-233° C. IR ṽ [cm$^{-1}$]=3289; 1716; 1577. FD-MS m/z (rel. Int.)=398.1 (1.71%; M⁺⁺). $^1$H NMR (300 MHz, DMSO) δ [ppm]=11.99 (bs, 1H, indole-NH), 11.07 (bs, 1H, imide-NH), 8.06 (d, $^3$J=2.6 Hz, 1H, indole-H), 7.44 (dd, J=4.7 Hz, J=8.8 Hz, 1H, indole-H), 6.94 (dt, J=2.3 Hz, J=9.1 Hz, 1H, indole-H); 6.7 (s, 2H, Ar—H), 5.91 (dd, J=2.1 Hz, J=10.7 Hz, 1H, indole H), 3.67 (s, 3H, OCH$_3$), 3.43 (s, 6H, 2×OCH$_3$).

(2) 3-(5-Fluoro-1H-indol-3-yl)-4-(4-hydroxy-3,5-dimethoxyphenyl)-maleimide To aluminium chloride (35 mmol) in DCM was added slowly 3-(5-Fluoro-1H-indol-3-yl)-4-(3,4,5-trimethoxyphenyl)-maleimide (10) (1.2 mmol) in DCM and the mixture was stirred for 4 h at ambient temperature. After completion, 20 ml water was added (0-3° C.) and the mixture was extracted with ethyl acetate. The organic phase was washed with water and brine, dried over MgSO₄ and concentrated and purified by column chromatography (PE/EE) to afford the product (0.8 mmol; 67%). $^1$H NMR (300 MHz, DMSO) δ [ppm]=11.92 (bs, 1H, indole-NH), 10.98 (bs, 1H, imide-NH), 8.85 (s, 1H, indole-H), 7.98 (s, 1H, indole-H), 7.44 (dd, J=4.56 Hz, J=9.03 Hz, 1H, indole-H), 6.88 (m, 1H, indole-H); 6.74 (s, 2H, Ar—H), 6.08 (d, J=8.20 Hz, 1H, indole-H), 3.43 (s, 6H, 2×OCH₃). Anal. calcd for $C_{22}H_{19}FN_2O_6 \times 0.5 H_2O$: C, 61.38; H, 4.12; N, 7.16. Found: C, 61.07; H, 4.40; N, 6.84.

For the following tests compounds (Ia) to (Id) as shown above were used in comparison to the following non-fluorinated compounds (IIa), (IIb) and (IId):

(IIa)

(IIb)

(IId)

(IIe)

The effect of test compounds on the activity of the protein kinases GSK-3β, VEGFR-2 and FLT-3 was evaluated based on half maximal inhibitory concentration ($IC_{50}$) values determined by Eurofins Pharma Discovery Services UK Limited, Gemini Crescent, Dundee Technology Park, Dundee, DD2 1SW (KinaseProfiler™). Detailed information can be found at: http://www.eurofins.com/pharma-services/pharma-discovery-services/services/in-vitro-pharmacology/kinases/biochemical.aspx. The assays are also described in Biochem. J. (2013) 451, 313-328. The results are given in the following table 1.

TABLE 1

| compound | R₁ | R₂ | VEGFR-2 ($IC_{50}$ [nM]) | GSK-3β | FLT-3 |
|---|---|---|---|---|---|
| IIb | ⁓⁓OH | H | 153 | 3 | 554 |
| Ib | ⁓⁓OH | F | 79 | 3 | 66 |
| If | ⁓⁓⁓OH | F | 168 | 3 | 84 |
| IIe | ⁓⁓⁓OH | H | 920 | 2 | 556 |

As can be seen, the fluorine-substituted compounds Ib and If of the invention exhibit a comparable effect as to GSK-3β and a significantly higher effect in inhibiting the activity of VEGFR-2 and FLT-3 as compared to the corresponding compound without fluorine substitution.

In a further experiment the metabolic conversion of compounds (Ia) and (IIa) was evaluated according to the following procedure:

The test compounds were incubated in the reaction mixture given below with rat liver microsomes (Corning). For this purpose the reaction mixture (components 1-5, see below) was preincubated for 10 minutes at 37° C. The reaction was started with the addition of 10 µl of the test compound followed by incubation at 37° C. for 0-300 minutes, respectively. At each time point, 50 µl of the mixture were removed, added to 250 µl of ice cold acetonitrile and vortexed immediately. After centrifugation, the acetonitrile solution was analyzed by RP-HPLC-MS/MS system.

Reaction Mixture:
1. Magnesiumchloride hexahydrate 50 µl
2. Glucose-6-phosphate 50 µl
3. NADP$^+$ 50 µl
4. Glucose-6-phosphate-dehydrogenase: 10 µl
5. Microsomes: 50 µl
6. Compounds: 40 µM (10 µl of 4 mM solution in ethanol)

Total volume: 1000 µl in 0.1 M Trizma-buffer (pH 7.4 at 37° C.)

RP-HPLC-MS System:
Acquity UPLC®-Quattro Premier XE (MS) system by Waters
Column: BEH C18, 2.1×50 mm, 1.2 µm pore diameter, Waters
Inject volume: 10 µl
Solvent A: H$_2$O, NH$_4$-formiate 2 mM+0.1% formic acid
Solvent B: Methanol, NH$_4$-formiate 2 mM+0.1% formic acid
Flow regime: from 70% solvent A/30% solvent B to 100% Solvent A in 2.4 minutes, then 70% solvent A/30% solvent B for 0.8 minutes.

Figure 1:
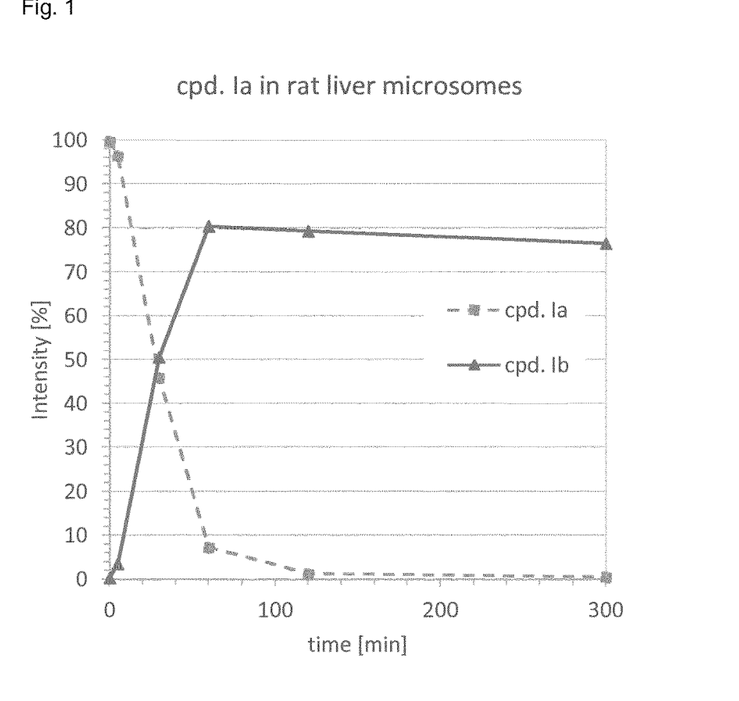
FIG. 1 shows the metabolization of compound Ia in rat liver microsomes over time.
Figure 2:
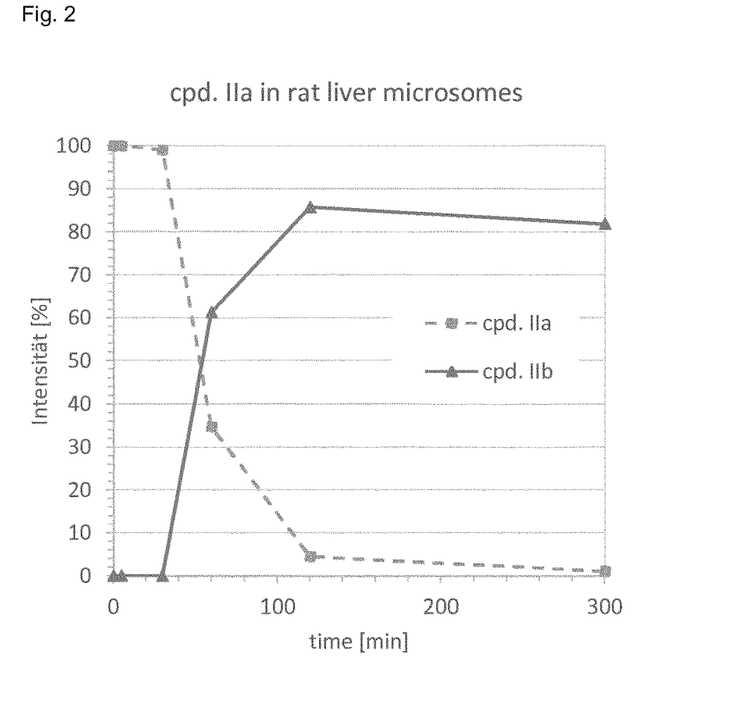
FIG. 2 shows the metabolization of compound IIa in rat liver microsomes over time.

The results for compound (IIa) are shown in FIG. 1 whereas the results for compound (IIa) are shown in FIG. 2. A time dependent degradation of both compounds and increasing concentration of the metabolite (Ib) and (IIb) can be seen. However, the metabolization of (Ia) is much faster than the metabolization of (IIa), i.e. (Ia) is largely metabolized after 1 h while it takes 2 h for (IIa) to metabolize to a comparable extent. As (Ib) is highly active, the faster metabolization is a significant advantage as the active principle is faster available as compared to (IIa).

Figure 3:
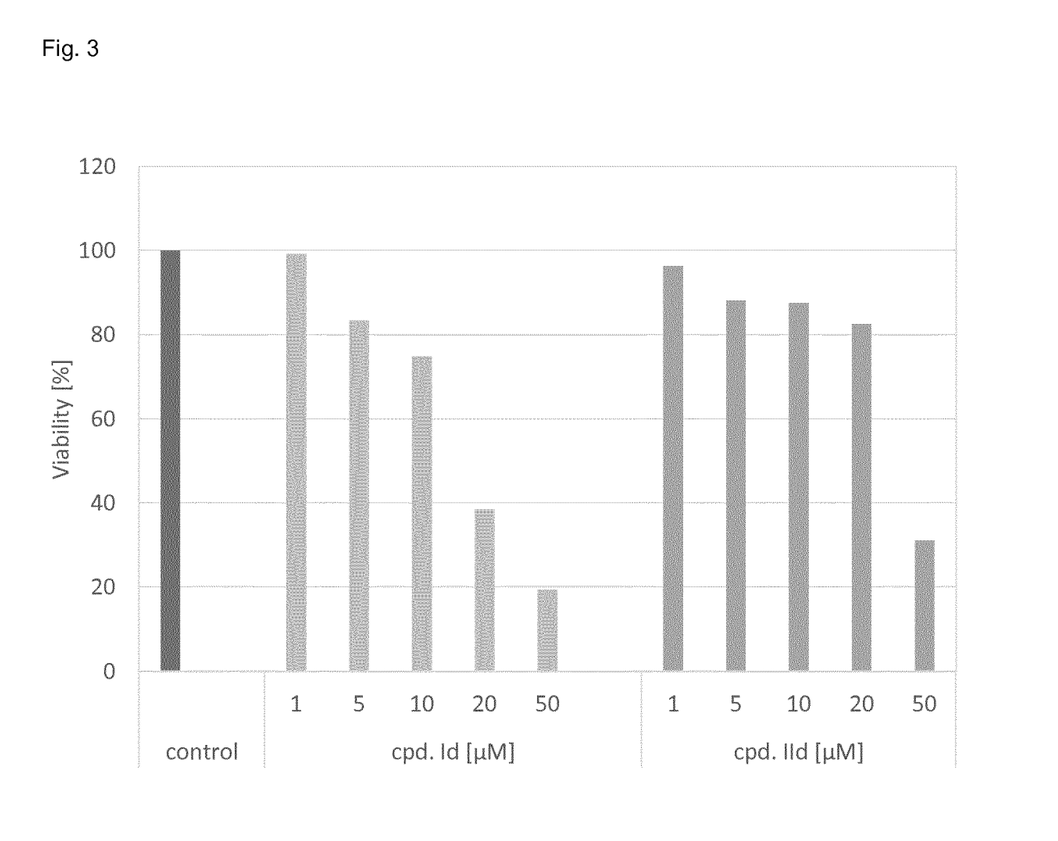
FIG. 3 shows the antiproliferative activity of compounds Id and IId against HT-29 human colon adenocarcinoma cells.

In a further experiment the antiproliferative activity against HT-29 human colon adenocarcinoma cells was determined by a MTT assay for compound (Id) of the invention and non-fluorinated compound (IId) using 3-(4,5-dimethylthiazol-2-yl)-2,5-diphenyltetrazolium bromide (MTT) as described previously (Mosmann, T. et al. (1983) J. Immunol. Methods 65, 55-63). Cells in the exponential growth phase were transferred to 96-well flat-bottom plates. 10,000 viable cells contained in 200 µl cell suspension were plated into each well and incubated over night. Cells were then exposed to various concentrations of test compounds (100 µl/well) for 3 days at 37° C. with 5% CO$_2$. Subsequently, 10 µl/well MTT stock solution (5 mg/ml; Biomol, Germany) was added and the cells were incubated at 37° C. with 5% CO$_2$ for 4 hours. 100 µl solubilization solution (10% SDS in 0.01 M HCl) was added and the cells were incubated at 37° C. with 5% CO$_2$ over night. Plates were read on an ELISA-Reader ELX 800 (BIO-TEK Software KC 4) at 562 nm absorbance. Each experiment was done in triplicate. The results are given in FIG. 3 which shows that compound (Id) of the invention has a time dependent, higher activity as compared to (IId) (the lower the viability of the target, the higher the activity).

The invention claimed is:

1. 3-(5-Fluoroindolyl)-4-phenylmaleimide compounds of formula (I)

wherein
R$^1$ is methoxy or hydroxyl; and
R$^2$ is 2-amino-4-methylbutanoyloxyethyl, 2-amino-4-methylbutanoyloxypropyl, hydroxyethyl, hydroxypropyl or H;
with the proviso that, if R$^2$ is H, R$^1$ is hydroxyl;
or a physiologically acceptable salt, a solvate or a solvate of a physiologically acceptable salt of the compounds of formula I.

2. The compound of claim 1 having formula (I) wherein R$^1$ is methoxy and R$^2$ is 2-amino-4-methylbutanoyloxyethyl, hydroxyethyl, or a physiologically acceptable salt, a solvate or a solvate of a physiologically acceptable salt of the compounds of formula I.

3. The compound of claim 1 having formula (I) wherein R$^1$ is hydroxy and R$^2$ is hydroxyethyl or H, or a physiologically acceptable salt, a solvate or a solvate of a physiologically acceptable salt of the compounds of formula I.

4. The compound of claim 1 having formula (I) wherein R$^1$ is methoxy or hydroxyl and R$^2$ is hydroxyethyl, or a physiologically acceptable salt, a solvate or a solvate of a physiologically acceptable salt of the compounds of formula I.

5. The compound of claim 1 having formula (Ia)

or a physiologically acceptable salt, a solvate or a solvate of a physiologically acceptable salt of the compounds of formula (Ia).

6. The compound of claim 1 having formula (Ib)

or a physiologically acceptable salt, a solvate or a solvate of a physiologically acceptable salt salts of the compounds of formula (Ib).

7. The compound of claim 1 having formula (Ic)

or a physiologically acceptable salt, a solvate or a solvate of a physiologically acceptable salt of the compounds of formula (Ic).

8. The compound of claim 1 having formula (Id)

or a physiologically acceptable salt, a solvate or a solvate of a physiologically acceptable salt of the compounds of formula (Id).

9. The compound of claim 1 having formula (Ie)

or a physiologically acceptable salt, a solvate or a solvate of a physiologically acceptable salt of the compounds of formula (Ie).

10. The compound of claim 1 having formula (If)

or a physiologically acceptable salt, a solvate or a solvate of a physiologically acceptable salt salts of the compounds of formula (If).

11. The compound of claim 1 having formula (Ig)

or a physiologically acceptable salt, a solvate or a solvate of a physiologically acceptable salt of the compounds of formula (Ig).

12. A pharmaceutical composition comprising one or more compounds of claim 1 and a pharmaceutically acceptable excipient.

13. The composition of claim 12, further comprising one or more additional chemotherapeutic agents.

14. The composition of claim 13, wherein the additional chemotherapeutic agent is selected from antineoplastic agents, multidrug resistance reversing agents, and biological response modifiers, and combinations thereof.

15. The composition of claim 13, wherein the additional chemotherapeutic agent is at least one topoisomerase I inhibitor.

16. The composition of claim 15, wherein the topoisomerase I inhibitor is irinotecan or topotecan or a mixture thereof.

17. A method for the treatment of adenocarcinomas which comprises administering an antitumorally effective amount of at least one compound according to claim 1 to a subject in need thereof.

18. The method of claim 17, further comprising the administration of an additional chemotherapeutic agent.

19. The method of claim 18, wherein the additional chemotherapeutic agent and the compound of formula (I) are administered sequentially, intermittently or simultaneously.

20. The method of claim 18, wherein the additional chemotherapeutic agent is selected from antineoplastic agents, multidrug resistance reversing agents, and biological response modifiers, and combinations thereof.

21. The method of claim 18, wherein the additional chemotherapeutic agent is at least one topoisomerase I inhibitor.

22. The method of claim 21, wherein the topoisomerase I inhibitor is irinotecan or topotecan or a mixture thereof.

23. The method of claim 17, wherein the method is a method for the treatment of colorectal adenocarcinoma.

\* \* \* \* \*